(12) United States Patent
Sun

(10) Patent No.: US 10,836,726 B2
(45) Date of Patent: Nov. 17, 2020

(54) AZO-QUATERNARY PYRIDINIUM SALTS WITH ACID-ENHANCED ANTIBACTERIAL EFFICACY, METHODS OF USE, METHODS OF SYNTHESIS, AND USES THEREOF

(71) Applicant: ADA Foundation, Chicago, IL (US)

(72) Inventor: Jirun Sun, Rockville, MD (US)

( * ) Notice: Subject to any disclaimer, the term of this patent is extended or adjusted under 35 U.S.C. 154(b) by 152 days.

(21) Appl. No.: 15/723,763

(22) Filed: Oct. 3, 2017

(65) Prior Publication Data

US 2018/0105495 A1 Apr. 19, 2018

Related U.S. Application Data

(60) Provisional application No. 62/408,826, filed on Oct. 16, 2016.

(51) Int. Cl.
| | | |
|---|---|---|
| *C07D 213/76* | (2006.01) | |
| *C07D 213/20* | (2006.01) | |
| *C08F 220/34* | (2006.01) | |
| *G01N 33/543* | (2006.01) | |
| *G01N 33/68* | (2006.01) | |
| *C08F 26/06* | (2006.01) | |
| *C08F 226/06* | (2006.01) | |
| *C08F 126/06* | (2006.01) | |

(52) U.S. Cl.
CPC ......... *C07D 213/76* (2013.01); *C07D 213/20* (2013.01); *C08F 220/34* (2013.01); *G01N 33/5438* (2013.01); *G01N 33/6887* (2013.01); *C08F 26/06* (2013.01); *C08F 126/06* (2013.01); *C08F 226/06* (2013.01); *G01N 2333/78* (2013.01)

(58) Field of Classification Search
CPC ... C07D 123/20; C07D 123/76; C08F 226/06; C08F 126/06; C08F 26/06
See application file for complete search history.

(56) References Cited

PUBLICATIONS

Garcia-Amoros, Jaume et al. "Fast Isomerizing methyl Iodide Azopyridinium salts for Molecular Switches" 2010 Organic Letters vol. 12 No. 15 p. 3514-3517 (Year: 2010).*
Nishida,K. et al, "Dyeing Properties of Reactive Azo Disperse Dyes and Reactive Azo Cationic Dyes derived from N-ethyl-N-β-vinyl-sulphonylethylanilin as the Coupling Component and 3- and 4-Aminopyridine as the Diazo Components" Sep. 1980 JSDC vol. 96 p. 481-485 (Year: 1980).*
Zapp,Eduardo et al "Liquid crystal and gold nanoparticles applied to electrochemical immunosensor for cardiac biomarker", 2014 Biosensors and Bioelectronics 59 p. 127-133 (Year: 2014).*

(Continued)

*Primary Examiner* — Ling Siu Choi
*Assistant Examiner* — David L Miller

(57) ABSTRACT

A new azo-type quaternary pyridinium salt (Azo-QPS) shows enhanced activity at acidic conditions (e.g., pH=5); in neutral or basic conditions, this new Azo-QPS shows a much lower level (2-50 times less) anti-bacterial activity. The use of such a "stimulus-enhance" antibiotic can response to the proliferation of bacteria directly. It helps reduce or prevent the build-up of potent antibacterial agents in the oral environment. The antibacterial properties of Azo-QPS are "activated" when the environmental pH becomes acidic; this acidic pH may be indicative of the accumulation of *Streptococcus mutans,* or the initiation of tooth decay.

8 Claims, 1 Drawing Sheet

(56) References Cited

PUBLICATIONS

Perez, D.; Baker, P.; Pintar, A., Sun, J., Lin, N., Lin-Gibson, S., Experimental and statistical methods to evaluate antibacterial activity of a quaternary pyridinium salt on planktonic, biofilm-forming, and biofilm states, Biofouling 2017, V. 33, No. 3, 222-234, http://dx.doi.org/10.

Zhou, H., Li, F., Weir, M., Hockun, X., Dental plaque microcosm response to bonding agents containing quaternary ammonium methacrylates with different chain lengths and charge densitities, J. of Dentistry 41 (2013), 1122-1131; Elsevier, http://dx.doi.org/10.

Extended European Search Report, dated Mar. 31, 2020.

* cited by examiner

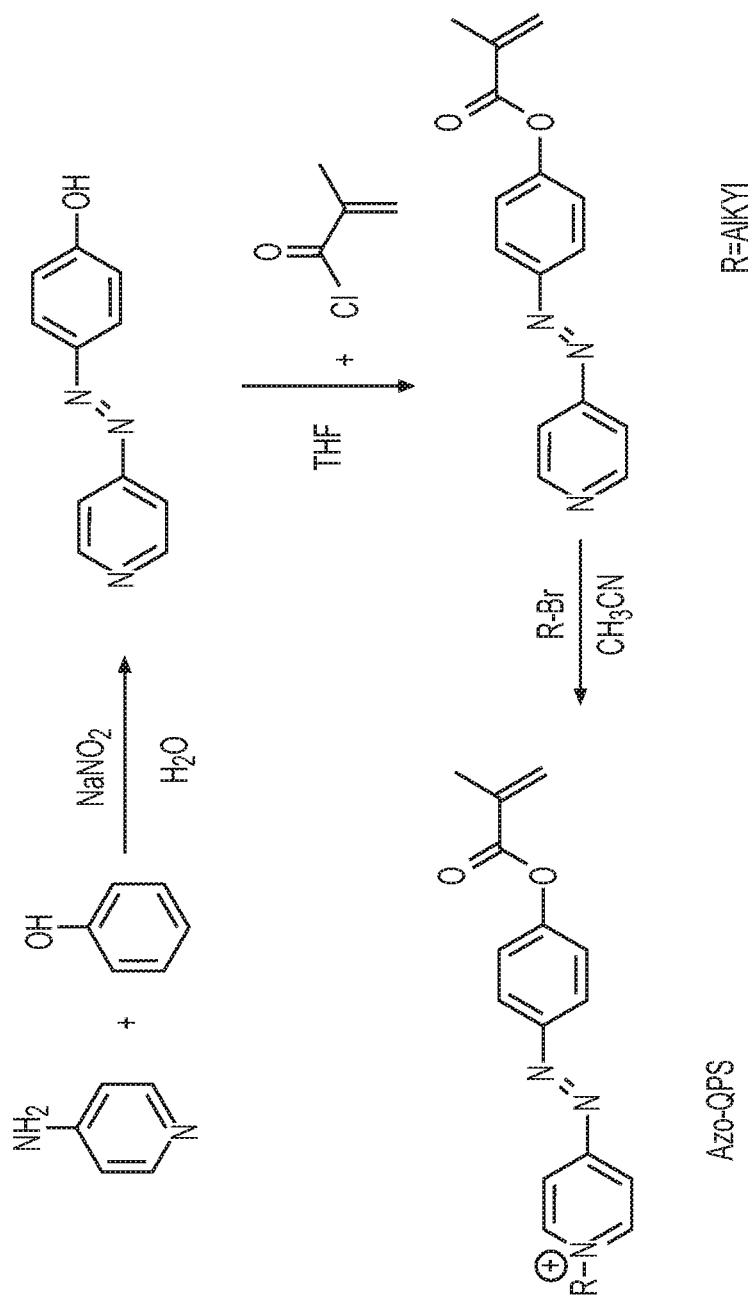

AZO-QUATERNARY PYRIDINIUM SALTS WITH ACID-ENHANCED ANTIBACTERIAL EFFICACY, METHODS OF USE, METHODS OF SYNTHESIS, AND USES THEREOF

RELATED APPLICATIONS

This application claims the benefit of U.S. Provisional Patent Application 62/408,826, filed Oct. 16, 2016, entitled Environment Activated Antibacterial Azo-Quarternary Pyridinium Salts, Methods of Use, Methods of Synthesis, and Uses Thereof, the content of which is incorporated by reference.

BACKGROUND

Antimicrobial resistance is the ability of a microbe to resist the effects of medication previously used to treat the microbe. More narrowly, antimicrobial resistance (sometimes called anti-bacterial resistance or antibiotic resistance) refers to resistance of bacteria to antibiotics. The World Health Organization states the such antibiotic resistance is a current threat in every region of the world and has the potential to affect anyone, of any age, in any country. Thus, antibiotic resistance—when bacteria change so antibiotics no longer work in people who need them to treat infections—is now a major threat to public health.

In oral environments, the bacteria *Streptococcus mutans*, is the primary causative agent in the formation of dental cavities. *Streptococcus mutans* is able to survive and thrive in an acidic/low pH (as low as pH 4) oral environment. In fact, in an oral environment, a sufficiently acidic pH is indicative of the accumulation of *Streptococcus mutans* and initiation of tooth decay. Quaternary ammonium salts (QAS) with antimicrobial activities have been developed to combat *Streptococcus mutans*. However, current formulations of these salts do not demonstrate both a high antibacterial effectiveness toward *Streptococcus mutans* and sensitivity toward varying environmental pH.

SUMMARY

Disclosed is a new azo-type quaternary pyridinium salt (Azo-QPS) that shows enhanced activity at acidic conditions (e.g., pH=5); in neutral or basic conditions, this new Azo-QPS shows a much lower level (2-50 times less) antibacterial activity. Such a "stimulus-enhance" antibiotic can respond directly to the proliferation of bacteria and can reduce or prevent the build-up of potent antibacterial agents in the oral environment. The antibacterial properties of Azo-QPS are "activated" when the environmental pH becomes acidic; this acidic pH may be indicative of the accumulation of *Streptococcus mutans*, or the initiation of tooth decay.

In an embodiment, a compound includes an azo-quaternary pyridinium salt (Azo-QPS) with groups $R_1$ and $R_2$, the compound having the formula:

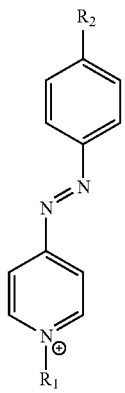

$R_1$ may be chosen from a group of functional moieties consisting of $-C_nH_{(2n+1)}$, $-C_nH_{(2n-1)}$, and their derivatives, where n is an integer preferably between 2 and 20. $R_2$ may chosen from a group consisting of $-OH$, $-NH_2$, $-NMe_2$, Alkyl, $-OCH_3$, $OC_2H_5$, and their derivatives. $R_2$ also may be chosen from a group consisting of polymerizable functional moieties, methacrylate, acrylate, styrene, vinyl benzyl and their derivatives.

DESCRIPTION OF THE DRAWINGS

FIG. 1 illustrates an example synthesis of the small organic molecule Azo-QPS-C16.

DETAILED DESCRIPTION

Antibacterial resistance presents severe health care challenges. In human dental (oral) environments, bacteria can cause tooth decay and associated problems. One such bacteria, *Streptococcus mutans*, is the primary causative agent in the formation of dental cavities; *Streptococcus mutans* is able to survive and thrive in an acidic/low pH (as low as pH 4) oral environment. Many quaternary ammonium salts (QAS) with antimicrobial activities have been developed recently to combat *Streptococcus mutans*. However, these current QAS formulations do not demonstrate both a high effectiveness towards *Streptococcus mutans* and a great sensitivity towards varying environmental pH.

To overcome limitations of current QAS formulations while addressing concerns related to anti-bacterial resistance, applicants developed, characterized, and tested a novel and non-obvious family of azo-type quaternary pyridinium salt (Azo-QPS) formulations. Azo compounds comprise, generally, the functional group $R'_1-N=N-R'_2$, in which $R'_1$ and $R'_2$ groups can be either aryl or alkyl.

Applicants hypothesized that the herein disclosed Azo-QPS formulations would show a high activity only at acidic conditions (e.g., pH=5) and that in neutral or basic conditions, the new Azo-QPS formulations would exhibit a much lower level (2-50 times lower) antibacterial activity. With these predicted characteristics, such "stimulus-enhanced" antibiotics (i.e., the new Azo-QPS formulations are "activated" only when the environmental pH becomes acidic, which, as noted above, indicates the accumulation of *Streptococcus mutans* and the initiation of tooth decay) can help reduce or prevent the build-up of potent antibacterial agents in the oral environment and thereby lessen the development of antibacterial resistance.

In particular, a family of Azo-QPS compounds was developed and characterized. The antibacterial activity of these Azo-QPS compounds towards Gram-positive (*Escherichia coli—E coli*) and Gram-negative (*Streptococcus mutans*) bacteria then was evaluated. The antibacterial efficacy of the herein disclosed Azo-QPS compounds has shown high sensitivity to changes within physiological pH ranges as a result of reversible assembly that can be controlled both by pH and redox reagents. An example structural formula for an Azo-QPS compound is shown below:

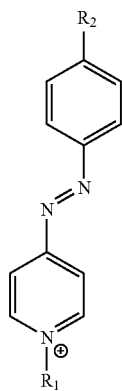

In this formulation $R_1$ is chosen from a group of functional moieties consisting of —$C_nH_{(2n+1)}$, —$C_nH_{(2n-1)}$, and their derivatives, where n is an integer between 2 and 20; and $R_2$ is chosen from a group consisting of —OH, —$NH_2$, —$NMe_2$, Alkyl, —$OCH_3$, $OC_2H_5$, and their derivatives. $R_2$ also may be chosen from a group consisting of polymerizable functional moieties, methacrylate, acrylate, styrene, vinyl benzyl and their derivatives.

An embodiment of the herein disclosed new azo-type quaternary pyridinium salt (Azo-QPS) was designed with a readily polymerizable methacrylate $R_2$ group; this Azo-QPS formulation exhibits high antibacterial effectiveness towards Gram-positive (*Escherichia coli*) and Gram-negative (*Streptococcus mutans*) bacteria. Similarly, when the $R_2$ group is one of acrylate, styrene or vinyl benzyl, the corresponding Azo-QPS formulation also should exhibit high antibacterial effectiveness towards Gram-positive (*Escherichia coli*) and Gram-negative (*Streptococcus mutans*) bacteria, and thus would be a candidate for readily producing antibacterial materials. In addition, the effectiveness of the new Azo-QPS formulations is sensitive to a varying environmental pH. Specifically, at lower pH (pH=5) conditions, the Azo-QPS formulations show much higher (2-50 times) antibacterial activity than at higher pH levels (pH=7-9, for example). Such disparity in antibacterial activity is due to the reversible electron reductions of Azo-QPS; the reversible electron reductions can be induced both chemically (e.g., by trimethylamine ($NEt_3$) and acetic acid ($CH_3COOH$)) (see the example structural formulation below) and electrochemically. This discovery shows great potential in renovating current bacterial drugs as the new Azo-QPS formulations help prevent the build-up of antibiotics, which in turn may serve as a solution to a universal problem of bacterial resistance to antibiotics.

In addition, the Azo-QPS formulations may serve as multifunctional immunosensors that not only have antibacterial properties, but also respond to redox reactions or antigen-antibody reactions, and quantify the concentration of antigens in saliva, blood, or aqueous solutions.

Possible uses for the Azo QPS formulations include:
Acting as an anti-bacterial drug with high efficacy (low µg/mL level) towards Gram-positive (*Escherichia coli*) and Gram-negative (*Streptococcus mutans*) bacteria.
Acting as an anti-bacterial linkage that can be integrated into polymeric materials. The vinyl functional group can act as the linker, and applicants have proven that methacrylate functional groups may be included without interfering or compromising the potent anti-bacterial activity of Azo-QPS.
The polymeric materials with Azo-QPS may be used as dental composites, other medical devices, biomaterials, and food-packaging materials, for example.
Acting as a sensor. The high sensitivity of Azo-QPS to both physiological pH levels and redox potentials makes it possible for Azo-QPS to function as an immunosensor and a pH sensor.

EXAMPLES

Example 1

Synthesis of (E)-1-hexadecyl-4-((4-(methacryloyloxy)phenyl)diazenyl)-pyridinium bromide (named Azo-QPS-C16)

General Information for synthesis and characterization. Commercially available materials purchased from Alfa Aesar (Tewksbury, Mass., USA), Sigma-Aldrich (Saint Louis, Mo., USA) and TCI America (Portland, Oreg., USA) were used as received. Proton and carbon nuclear magnetic resonance (1H and 13C NMR) spectra were recorded on a Bruker instrument (600 MHz, Billerica, Mass., USA) using 5 mm tubes. Chemical shifts were recorded in parts per million (ppm, δ) relative to tetramethylsilane (δ=0.00), dimethylsulfoxide (δ=2.50) or chloroform (δ=7.26). 1H NMR splitting patterns are designated as singlet (s), doublet (d), triplet (t), quartet (q), dd (doublet of doublets), and m (multiplets). High-resolution mass spectra (MS) were recorded on a JEOL AccuTOF (Peabody, Mass., USA) for ESI-TOF-MS analysis.

Azo-QPS-C16 is a small organic molecule. An example synthesis procedure is shown in FIG. 1.

Five (5) g (53.2 mmol) of phenol and 4 g (60 mmol) of sodium nitrite were dissolved in 20 mL 10% (w.t.) sodium hydroxide aqueous solution, and the mixture was stirred in an ice-bath at 0-4° C. The mixture was added dropwise to a pre-cooled solution made from 6 g (63.8 mmol) of 4-Aminopyridine in a hydrogen chloride aqueous solution. The reaction was stirred in the ice-bath for 30 minutes, and then stirred at room temperature overnight. The pH of the reaction was adjusted to 6-7 with ten percent by weight (10% (w.t.)) sodium hydroxide; the precipitation was collected by filtration, and dried in air. The azo product was used in the next step without further purification.

In this next step, 4 g (20.1 mmol) of the azo and 1.25 equivalent of trimethylamine was dissolved in tetrahydrofuran (THF). One (1) equivalent of methacryloyl chloride was added to the reaction dropwise. The reaction was stirred at room temperature for 2 hours. The Azo-QPS-methacrylate compound was purified by column chromatography with an 87% yield.

Finally, the Azo-QPS-methacrylate compound was refluxed with 1.5 equivalent of desired alkyl bromide in acetonitrile for three days. The resulting dark red product was further purified by recrystallization with ether and acetone, affording 48-56% yield of Azo-QPS-C16. Chemical shift of protons in 1H NMR (600 MHz, CDCl3) spectrum follows: δ 9.64 (d, J=6.0 Hz, 2 H), 8.30 (d, J=6.0 Hz, 2 H), 8.10 (d, J=6.0, 11.0 Hz, 2 H), 7.40 (d, J=16.0, 2 H), 6.42 (s, 1 H), 5.86 (s, 1 H), 5.11 (t, J=7.4 Hz, 2 H), 2.08 (m, 5 H), 1.33 (m, 26 H), 0.88 (m, 3 H) ppm; 13C NMR (600 MHz, CDCl3) δ 165.01, 160.42, 156.39, 149.86, 147.21, 135.34, 128.44, 126.27, 123.07, 120.50, 62.03, 32.11, 31.93, 31.17, 29.70, 29.69, 29.66, 29.64, 29.60, 29.51, 29.37, 29.10, 28.77, 26.15, 22.70, 18.32, 14.12 ppm. Hi-Res MS (ESI): m/z calcd. for C31H46N3O2+, 492.3585; found [M]+: C31H46N3O2+, 492.3599.

Example 2

Acid-enhanced Antibacterial Efficacy

Azo-QPS-C16 was effective on both Gram-positive (*Escherichia coli*) and Gram-negative (*Streptococcus mutans*) bacteria. The ability of bacteria to proliferate after exposure to Azo-QPS-C16 was characterized by adding growth medium and measuring the optical density (OD) at 600 nm every 15 minutes in pH 4.1, 5.8, and 7.9 buffer. Exposure to 2.5 µg/mL of Azo-QPS-C16 at pH 4.1 fully inhibited *E. coli* growth up to 19 hours. However, exposure at pH 7.9 required a much higher concentration (40 µg/mL) to inhibit cell growth. Obvious growth of *E. coli* was observed for all buffer control measurements including different pH values with and without dimethyl sulfoxide (DMSO). The pH dependence of bactericidal activity of Azo-QPS-C16 in terms of minimum bactericidal concentration (MBC) was evaluated by inoculating cultures onto a Lysogeny Broth (LB) agar plate after treating the cells with a twofold dilution series of Azo-QPS-C16. As pH increased, the MBC correspondingly increased. A 16-fold difference in MBC was observed between pH 4.1 and pH 7.9.

The inventor observed similar pH-sensitive antibacterial activity of Azo-QPS-C16 towards the Gram-positive, lactic acid producing, cariogenic bacteria *S. mutans*. According to MBC assessments, Azo-QPS-C16 is 8-fold more effective against *S. mutans* in acidic than in mildly basic conditions.

Bacterial strains and growth conditions. *Streptococcus mutans* (*S. mutans*, UA159) and *Escherichia coli* (*E. coli*, K12) were purchased from ATCC (American Type Culture Collection, Manassas, Va., USA). Todd Hewitt Broth (THB), and Lysogeny Broth (LB) powder and agar were purchased from BD (Becton, Dickinson and Company, Franklin Lakes, N.J., USA). Planktonic cultures were inoculated from 25% (by volume) glycerol frozen stocks stored at −80° C. *E. coli* cultures were grown in LB at 37° C. in a shaker-incubator. *S. mutans* cultures were grown in THB at 37° C. with 5% (by volume) $CO_2$ overnight.

Bacterial growth curves. Overnight cultures of *E. coli* and *S. mutans* were diluted directly into buffers with different pH values (100 mmol/L, pH 4.1 sodium acetate buffer, pH 5.8 sodium phosphate buffer, and pH 7.9 sodium phosphate buffer) to an optical density at 600 nm (OD600) of approximately 0.001.

In a 96-well plate, 2 µL of Azo-QPS-C16 at various concentrations in dimethyl sulfoxide (DMSO) were added to 98 µL of bacteria suspension per well for a final concentration ranging from a 2-fold dilution series between 40 to 1.25 µg/mL of Azo-QPS-C16. After 45 min of treatment at room temperature, 10 µL from each well were transferred to a new 96-well plate already containing 100 µL growth media per well to measure the growth curves. *E. coli* were cultured at 37° C., and the OD600 of each well was measured by a Tecan Spark microplate reader (Männedorf, Switzerland) every 15 minutes for up to 19 hours, with 30 seconds shaking before each measurement. *S. mutans* were grown at 37° C. with 5% CO2, and the OD600 of each well was measured periodically using a Molecular Devices (Sunnyvale, Calif.) SpectraMax M5 microplate reader. All experiments were conducted in triplicate, and repeated at least three times on different days.

Minimum bactericidal concentration (MBC) determination. MBC values were determined by agar colony formation. The same treatment was applied to the bacteria as for the growth curve measurement. 5 µL of the suspended cells from each well were spotted onto an agar plate and incubated for 48 hours to allow colony formation, and the presence or absence of bacterial growth was determined by naked eye. All experiments were conducted in triplicate and repeated at least three times on different days.

Example 3 pH Sensitive Physicochemical Properties

Azo-QPS-C16 exhibits pH-sensitive physicochemical properties that correlate with its acid-enhanced antibacterial activity. Aqueous solutions of Azo-QPS-C16 (0.01 mmol/L, 5.7 µg/mL) appear clear orange and purple in acidic and basic conditions, respectively, consistent with the red-shift observed in UV-vis spectra. UV-vis spectra were recorded on a Thermo Spectronic Genesys 5 UV-vis spectrophotometer (Thermo Scientific, Waltham, Mass. USA) using quartz cuvettes with 1 cm path length at 298 K after baseline correction. Intensification of a peak centered at 554 nm and simultaneous decrease of a peak at 347 nm are proportional to a change in pH from 4.1 to 7.9. Similar absorbance peaks were detected in DMSO (0.05 mmol/L, 28.6 µg/mL), where molar equivalents of base, e.g., triethylamine (TEA) were added; the decrease of peak intensity at 347 nm is proportional to an increasing mole ratio of TEA to QPS.

Example 4

Base-induced Switchable Assembly

In addition to color changes, assembly of Azo-QPS-C16 at various pH values was observed with dynamic light scattering (DLS). Particles with an average hydrodynamic diameter of 51±19 nm formed in mildly basic conditions, occurring simultaneously with the appearance of the absorbance peak at 554 nm. No particles were found in pH 4.1 buffer. Reversible switching between acidic and basic conditions in DMSO was demonstrated over three cycles through successive additions of 5 molar equivalents TEA and then trifluoroacetic acid (TFA). One cycle corresponds to addition of base and acid. In base and acid, respectively, the absorbance at 554 nm increased and then decreased, and the particles formed and disassembled.

The short chain Azo-QPS-C2 showed similar switchable assembly in terms of appearance and particle size distribution. Its UV-vis spectra had two peaks at 350 nm and 540 nm, comparing to 347 nm and 554 nm in the spectra of Azo-QPS-C16. DLS determined that these two compounds had the same hydrodynamic diameter and particle size distribution when base was added. Such a good match indicates that the chain length of the tails has minimal impact on the assembly of these compounds.

Dynamic light scattering (DLS) was performed using a Nicomp 380 ZLS DLS system (Particle Sizing Systems Inc., Santa Barbara, Calif.). Samples were contained in disposable glass culture tubes. Prior to sample loading, the tubes were blown with nitrogen gas and filled with 0.4 mL of the dye sample. The tubes were sealed using parafilm and then centrifuged at 14 000 rpm (19 000 g) for 5 minutes to separate larger particles and dust. Samples were placed in the instrument and allowed to attain thermal equilibrium. Autocorrelation function was acquired for 3 minutes at 173° scattering angle. A Laplace inversion based Nicomp routine was used to find the distribution of decay rates. The decay rates are linked to the effective sphere hydrodynamic diameters by the appropriate equations. The size distribution is reported as a discrete set of diameter bins and corresponding intensity weighted fractions as probabilities assigned to diameter bins.

Example 5 pH Sensitivity in Adsorbed Films

The effect of pH on potential was examined with cyclic voltammetry (CV) to understand the role of protonation/deprotonation in adsorbed Azo-QPS-C16 films, as azobenzene and its derivatives are electrochemically active. The redox couple likely arises from the reduction of azobenzene to hydrazobenzene and vice versa. Adsorption of Azo-QPS-C16 on glassy carbon was evaluated at varying concentrations by adding 10 µL aliquots of 1 mmol/L (572 µg/mL) Azo-QPS-C16 in DMSO to 10 mL of 100 mmol/L phosphate buffer, pH 6.8. A redox couple appears with an average peak potential, $E_{1/2}$, near −50 mV vs. Ag/AgCl. The peak current increases at higher concentrations, as expected. However, the peaks become narrower at concentrations above 0.04 mmol/L (23 µg/mL), suggesting an adsorption process occurring at higher concentrations. Based on the shape of the peaks and the fact that the ratio of the anodic peak current, $i_{pa}$, to the cathodic peak current, $i_{pc}$, is greater than unity, the dominant behavior may be weak adsorption of the reactant below 0.04 mmol/L and then adsorption of the product at concentrations higher than 0.05 mmol/L (29 µg/mL). Also, the average peak potential, $E_{1/2}$, shifts positive, and the difference in the peak potentials, $\Delta E$, becomes narrower at higher Azo-QPS-C16 concentrations.

When the electrode was removed from the 0.1 mmol/L (57 µg/mL) Azo-QPS-16 solution, rinsed with water to remove any weakly bound compound, and then immersed in fresh buffer, a redox couple appears at −50 mV vs. Ag/AgCl. A plot of $i_{pc}$ and $i_{pa}$ vs. sweep rate, v, is linear, confirming that the species adsorbs. As with adsorption from buffer, a layer forms on the electrode surface in DMSO. The film was stable for at least an hour although some desorption occurred within 45 minutes of immersion.

Given that $i_p = (n^2 F^2 v A \Gamma)/(4RT)$ for an adsorbed electrochemically reversible system, where n is one electron, F is Faraday's constant (96,485 C/mol), v is sweep rate in V/s, A is the electrode area in cm², $\Gamma$ is the surface coverage in mol/cm² R is the molar gas constant (8.314 J/mol/K), and T is the temperature in K, the surface coverage of Azo-QPS-16 formed in the DMSO/buffer system, was estimated to be 200 pmol/cm², similar to that of a azo pyridinium compound with an eighteen-carbon chain in Langmuir-Blodgett films. The surface coverage obtained in DMSO/buffer was larger than that in DMSO (60 pmol/cm²), possibly due to stronger interactions between glassy carbon and Azo-QPS-C16 in water. The voltammetry of an adsorbed layer was examined in buffers of varying pH values similar to those used in the UV-vis and DLS measurements. Plotting $E_{1/2}$, vs. pH reveals a slope of −61 mV/pH unit, indicating a one proton per electron transfer process.

Cyclic voltammetry (CV). The working electrode was a 5-mm glassy carbon disk (0.79 cm²) polished with 1 µm alumina and then rinsed with copious amounts of water. The cell was a glass vial with a Pt auxiliary electrode and an Ag/AgCl/1 mol/L KCl reference electrode in a 3% agar+0.2 mol/L $KNO_3$ salt bridge. Glassware was cleaned by soaking in 3 mol/L $HNO_3$ overnight. CV was performed using the potentiostat of a Model 920D Scanning Electrochemical Microscope System (CH Instruments, Austin, Tex.).

Example 6

Label-free Electrochemical Methods for Different Biomarkers

The highly sensitive electrochemical (HSEC) for quantification of cardiac troponins (cTns) is based on changes in the electrochemical redox response of Azo-QPS-16 due to the interaction of cTnT and its antibody (TnT is a tropomyosin-binding subunit that regulates the interaction of troponin complex with thin filaments). The response is evaluated through electrochemical analytical methods: cyclic voltammogrammetry (CV) and square wave voltammogrammetry (SWV). The level of cTnT is reflected by the change of peak current of the Azo-QPS-16 adsorbed on the electrodes. Specifically, the working electrode will be coated by Azo-QPS-16, monoclonal antibody of cTnT for specific binding, and other sensitivity enhancing components including metal nanoparticles and chitosan. High concentrations of cTnT will increase the amount of protein attached on the electrode through antigen-antibody interaction, hence decreasing the electron transfer and peak current. The change in peak current is proportional to the concentration of cTnT in solution. Their mathematic correlation is defined by the antigen-antibody interaction, the design of the biosensor, and the experiment parameters, which will be optimized through experiments. A calibration cure was established to determine the concentration of cTnT in both PBS and pooled human saliva. This HSEC assay is a label-free process, and requires no treatment to the specimen. Through selection of antibody and implementing the corresponding calibration curves, the HSEC assay may be used in quantification of other biomarkers such as cardiac troponin I (inhibitory, cTnI) and other antigens.

Example 7

Chemistry of Assembly in Solutions

The chemistry revealed by NMR spectra confirms the key role of the phenyl-azo-pyridinium core in the assembly of Azo-QPS-C16/2. In addition, NMR spectra suggest that there are interactions between these compounds and the base. The spectrum of the mixture differs in a number of ways from that of the components. First, the peaks of protons on the aromatic rings and the first carbon of the QPS's tail yield very broad resonance signals; second, the protons on TEA are unobservable; third, no peak shift or change in integration are identified in the peaks of the other protons; and finally, no new peaks appear. Peak broadening and unobservable protons are likely due to assembly, which has been reported in supramolecular gels formed by low molecular weight species and agrees well with the particle formation determined by DLS. The assembly significantly increases the correlation time, consequently, leads to a very short transversal relaxation time, and very broad or unobservable signals. Moreover, the lack of TEA protons suggests that it participates in the assembly. TEA is a base and may interact with the Azo-QPS-C16 which is weakly acidic, pKa=5.33. The product of this interaction may be a chemical complex formed by the base and the Azo-QPS-C16. Based on the above NMR results combined with the base-induced red-shift in UV-vis spectra and assembly determined by DLS, the inventor believes that the interaction of TEA with Azo-QPS-C16 triggers assembly of tightly stacked π-conjugated cores, formed by two or more Azo-QPS-C16 molecules and the base. A model is predicted. This model uses a sandwich stacking conformation where the cores of the trans-isomer of Azo-QPS-C16 molecules are aligned in parallel. Further, the Azo-QPS-C16 molecules are packed with an alternating head-to-tail arrangement that minimizes the potential repulsion among the QPS moieties due to the positive charge of the pyridinium salt. This stacking model also maximizes the participation of TEA as its interaction with the Azo-QPS-C16 is most likely taking place close to the QPS moieties. The broadening resonance signals at 4.69 ppm in d-DMSO (5.11 ppm in $CDCl_3$), which belong to the protons on the first carbon of the pyridinium tail, strongly suggest such a possibility. As a result of charge repulsion and potential steric hindrance, head-to-tail arrangement is more favored than head-to-head or tail-to-tail arrangements and is likely to create the most impenetrable packing of the phenyl-azo-pyridinium core. Furthermore, TEA and its interaction with Azo-QPS-C16 molecules may also serve as a shutter to the access of the already tightly stacked core, thus isolating the core from the rest of the Azo-QPS-C16 molecules. Consequently, distinct observability of resonance signals is detected by NMR spectrometer. Finally, the interaction and the condensed stacking redistribute the positive charge of the QPS moiety within the assembly. The charge of the assembly (n+) is related to the number (N) of the participating Azo-QPS-C16 molecules and the participation of the base moieties.

Example 8

Correlated but Different Mechanism for pH-sensitivity and Acid-enhanced Antibacterial Efficacy The above results demonstrate that Azo-QPS-C16 is multifunctional and pH-sensitive in both solutions and adsorbed films. In solution, the pH-sensitivity is triggered by acid-base interaction and leads to different assembly stages of tightly stacked π-conjugated phenyl-azo-pyridinium core and base. The participation of base moieties may be $OH^-$ ion or its derivatives in aqueous solutions or moisture-containing solvents. In adsorbed films, the pH-sensitivity is due to the redox couple that likely arises from the reduction of azobenzene to hydrazobenzene and vice versa. In both states, the pH sensitivity is closely interrelated to the chemistry of the phenyl-azo-pyridinium core. The chain length of the QPS tail has minimal impact on the pH-sensitivity in solutions. However, the long carbon chain is vital to the acid-enhanced antibacterial efficacy, which is determined by a combination of multiple factors including the amphiphilic properties, cations, charge density and counter ions. In acidic conditions, the MBC of Azo-QPS-C16 for E. coli and S. mutans was 2.5 µg/mL and 1.25 µg/mL, respectively. In comparison, its short chain analog (Azo-QPS-C2) did not inhibit bacterial growth even at a concentration that was 400 to 800 times higher. Such distinct differences in antibacterial efficacy corresponding to the chain length not only validate the importance of the long-chain carbon tail in providing the needed amphiphilic properties of a strong antibacterial QPS, they also offer a tool to design and prepare pH-sensitive materials with a broad range of antibacterial efficacy. Moreover, in mildly basic conditions, Azo-QPS-C16 molecules interact with the base to form nanoparticles with an average hydrodynamic diameter of 51±19 nm containing tens of Azo-QPS-C16 molecules. Assuming each Azo-QPS-C16 molecule and one particle as individual effective antibacterial site, adjusting the pH changes the number of free molecules and their assemblies, which controls the number of effective sites and thus the antibacterial activity.

I claim:
1. An azo compound, comprising:
a quaternary pyridinium salt; and
groups $R_1$ and $R_2$, the azo compound having the formula:

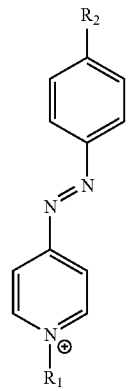

wherein $R_1$ is attached to the nitrogen of pyridinium salt and is selected from a first group of functional moieties consisting of $—C_nH_{(2n+1)}$, and $—C_nH_{(2n-1)}$, wherein n is an integer between 6 and 18;
wherein $R_2$ is attached to the benzene ring and is selected from a second group consisting of —OH, alkyl, $—OC_mH_{(2m-1)}$, and $OC_mH_{(2m+1)}$, wherein m is an integer between 1 and 8;
wherein a selection from the first group and a selection from the second group produces a polymerizable vinyl monomer; and
wherein $R_2$ may be substituted by a polymerizable functional moiety $R_3$ selected from a third group consisting of methacrylate, acrylate, styrene, and vinyl benzyl, wherein the substitution replaces a H atom.

2. The azo compound of claim 1 acting as an antibacterial drug towards both Gram-positive and Gram-negative bacteria.

3. The azo compound of claim 1 acting as an antibacterial drug with a higher efficacy (lower µg/mL level) towards Gram-positive and/or Gram-negative bacteria in acidic environment of pH <6, than in neutral and basic environments.

4. The azo compound of claim 1 acting as a pH sensor to determine pH values between 4 and 8.

5. The azo compound of claim 1 acting as a redox sensor to determine a level of oxidant and reducing agents.

6. The azo compound of claim 1 acting as a part of immunosensor to quantify an antibody-antigen interaction.

7. The azo compound of claim 1 as an antibacterial agent integrated into polymeric materials or particles by covalent bonding or through non-covalent bonds.

8. The azo compound of claim 1 as a pH sensor integrated into polymeric materials or particles by covalent bonding or through non-covalent bonds.

* * * * *

UNITED STATES PATENT AND TRADEMARK OFFICE
CERTIFICATE OF CORRECTION

Page 1 of 1

PATENT NO. : 10,836,726 B2
APPLICATION NO. : 15/723763
DATED : November 17, 2020
INVENTOR(S) : Jirun Sun It is certified that error appears in the above-identified patent and that said Letters Patent is hereby corrected as shown below:

In the Specification

Column 1, Line 16, after the paragraph titled "RELATED APPLICATIONS," insert the following:
--STATEMENT OF FEDERALLY SPONSORED RESEARCH
This invention was made with government support under grant U01 DE023752 awarded by the National Institutes of Health. The government has certain rights in the invention.--

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*